United States Patent
Mathis, Jr. et al.

[11] Patent Number: 5,372,813
[45] Date of Patent: Dec. 13, 1994

[54] SUBSTITUTED 6-NITROQUIPAZINES, METHODS OF PREPARATION, AND METHODS OF USE

[75] Inventors: Chester A. Mathis, Jr., Pittsburgh, Pa.; Anat Biegon, Rohovot, Israel; Scott E. Taylor, Pleasant Hill; Joel D. Enas, Pittsburg, both of Calif.

[73] Assignee: The Regents, University of California, Oakland, Calif.

[21] Appl. No.: 994,825

[22] Filed: Dec. 22, 1992

[51] Int. Cl.$^5$ .................. A61K 49/00; G01N 33/567; C07D 401/00
[52] U.S. Cl. .................. 424/1.85; 436/504; 544/363
[58] Field of Search .................. 424/1.1, 1.85, 1.89; 546/159, 160, 180; 544/363; 436/504

[56] References Cited

U.S. PATENT DOCUMENTS 3,728,351  4/1973  Counsell et al. .................. 260/288
3,929,907  12/1975  Janzon et al. .................. 260/619
4,784,958  11/1988  Glossman .................. 436/504

FOREIGN PATENT DOCUMENTS 0435192  7/1991  European Pat. Off. ..... G01N 33/94

OTHER PUBLICATIONS

Mathis et al., "[125I]5-Iodo-2-nitro-2-piperazinyl-quinoline . . . ," *European Journal of Pharmacology*, 210(1), 103-4, 1992.

*Primary Examiner*—Robert L. Stoll
*Assistant Examiner*—Lara E. Chapman
*Attorney, Agent, or Firm*—Paul R. Martin; Kathleen S. Moss; Pepi Ross

[57] ABSTRACT

Disclosed is a substituted 6-nitroquipazine of the formula

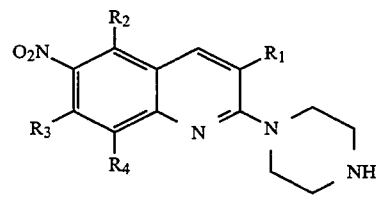

wherein $R_1$, $R_2$, $R_3$, and $R_4$ are each selected from the group consisting of H, Fl, CL, Br, I, $CF_3$, $CH_2CH_2F$, $CH_3$, $CH_2CH_3$, and $-CH(CH_3)_2$, and wherein one of $R_1$, $R_2$, $R_3$, and $R_4$ is other than H.

Also disclosed is a method for measurement of serotonin uptake sites in a sample, in which a radioligand is incubated with a sample and then the radioactivity of the radioligand bound to the sample is determined, utilizing a radio labeled substituted 6-nitroquipazine as the radioligand. Also disclosed is a method of manufacture and method of use.

16 Claims, 5 Drawing Sheets

SUBSTITUTED 6-NITROQUIPAZINES, METHODS OF PREPARATION, AND METHODS OF USE

BACKGROUND OF THE INVENTION

This invention was made with Government support under Contract No. DE-AC03-76SF00098 between the U.S. Department of Energy and the University of California for the operation of Lawrence Berkeley Laboratory. The Government has certain rights in this invention.

1. Field of the Invention

The present invention relates to certain substituted 6-nitroquipazines, to methods for their preparation, to radiolabeled derivatives thereof, and methods of use.

2. Related Art

In the treatment of mental disease, particularly depression, certain types of drugs have been found to be efficacious over the years. In particular, the so-called "tricyclic" compounds such as imipramine, amitriptyline, nortriptyline, and others have been used to counter the effects of depression. The mode of action of the tricyclic drugs appear to be that of an inhibitor of monoamine uptake, i.e., a 5-HT (5-hydroxytryptamine) uptake inhibitor.

The tricyclics and some new anti-depressant drugs not only inhibit monoamine uptake, but also bind directly with some neurotransmitter receptors. Antagonism of the receptor function is believed to contribute to certain side effects of anti-depressant drugs, such as dry mouth, dizziness, blurred vision, constipation, urinary retention, tachycardia, and memory disfunction. Antagonism of central $H_1$ histamine receptors may contribute to sedation or drowsiness and also to the weight gain associated with certain anti-depressants.

Because of the side effects of tricyclics, pharmaceutical companies are constantly on the lookout for more specific 5-HT uptake inhibitors which do not have the same side effects as the tricyclic compounds.

A series of more or less selective 5-HT uptake inhibitors has appeared in the literature in recent years. One of such compounds is fluoxetine, whose chemical name is (±)-N--Methyl-3-Phenyl-3-[($\alpha\alpha\alpha$-trifluoro-p-tolyl)oxy] propylamine. This compound, in therapeutic form, is known as Prozac.

Fluoxetine, because of its 5-HT uptake inhibitor specificity, does not have the common side effects associated with tricyclic amines.

Because of its selective affinity for the serotonin-uptake carrier, fluoxetine has been used as a radioligand to label the carrier.

The inhibition of serotonin uptake by fluoxetine is believed to cause an increase in concentration of serotonin in the synaptic cleft, since neuronal reuptake is the physiological means of removing serotonin from that cleft.

When compared with certain tricyclic amine drugs, fluoxetine has equal anti-depressant efficacy with fewer total side effects and dropouts among fluoxetine-treated patients. Fluoxetine performs as well as the tricyclic anti-depressants in relieving the symptoms of depression and is associated with a lower dropout rate due to adverse effects.

Another compound which has been found to be effective in binding of serotonin uptake sites in a sample is 6-nitroquipazine. This compound is described in European patent application number 90125092.8, filed Dec. 21, 1990. (European patent application publication number 0435192A2.) In this patent application it is disclosed that the measurement of serotonin uptake sites in a sample can be improved by using tritium-labeled 6-nitro-2-N-piperazinylquinoline or an acid addition salt thereof as the radioligand. As stated in that patent application, the termination of the effects of serotonin in synaptic function occurs in two ways, i.e., by an uptake process and by metabolism of the transmitter. Although the details of serotonin metabolism have been clearly established, the process is believed to play a minor role in terminating the action of serotonin at the synaptic cleft. The most likely terminating process is believed to be the reuptake of serotonin by the pre-synaptic terminal. Thus, serotonin uptake sites, which exist in the pre-synaptic nerve terminal, play an important role in regulating the serotonin content in the synaptic cleft.

It has been reported that there is a reduced density of serotonin uptake sites in the brain tissue of depressed patients and Alzheimer's disease. Therefore the study of serotonin uptake sites in the brain's of people with these diseases is useful for the diagnosis and therapy of these diseases.

One means of making these measurements is by means of radio receptor assay. Radio receptor assay is a method for measuring the radioactivity of a radioligand bound to sample after incubating the radioligand and sample.

Efforts are constantly being made, however, to discover new compounds which are more efficacious in binding to serotonin uptake sites, and thereby inhibiting 5-HT uptake in the synaptic cleft.

SUMMARY OF THE INVENTION

It is an object of this invention to provide certain substituted-6-nitroquipazines which have high affinity and high specificity for serotonin uptake sites.

It is a further object of this invention to provide a method for making such compounds.

It is a further object of this invention to provide radio labeled derivatives of substituted 6-nitroquipazines for use as radioligands.

It is a further object of this invention to provide an improved method for measuring serotonin uptake sites using a radio labeled substituted-6-nitroquipazine as a radioligand in measuring the radioactivity bound to serotonin uptake sites after reacting the radioligand and sample.

The 6-nitroquipazine compounds of this invention have the formula

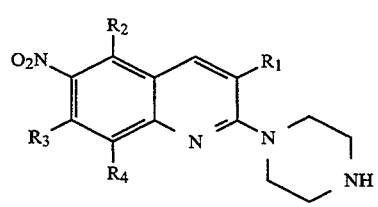

wherein $R_1$, $R_2$, $R_3$, and $R_4$ are each selected from the group consisting of H, Fl, CL, Br, I, $CF_3$, $CH_2CH_2F$, $CH_3$, $CH_2CH_3$, and $—CH(CH_3)_2$, and one of $R_1$, $R_2$, $R_3$, and $R_4$ is other than H.

Radiolabeled derivatives of these compounds are used as the radioligand. In a preferred embodiment $R_1$, $R_3$, and $R_4$ is H, and $R_2$ is I, wherein I is $^{125}I$ or $^{123}I$.

As used herein, the term substituted 6-nitroquipazine refers not only to the base compound, but to acid addition salts thereof.

Suitable acids for the acid addition salts are inorganic acids such as hydrochloric acid, sulfuric acid, nitric acid, and the like, as well as organic acids including acetic acid, oxalic acid, citric acid, fumaric acid and the like.

DETAILED DESCRIPTION OF THE INVENTION AND PREFERRED EMBODIMENTS

General Methods

Figure 1:
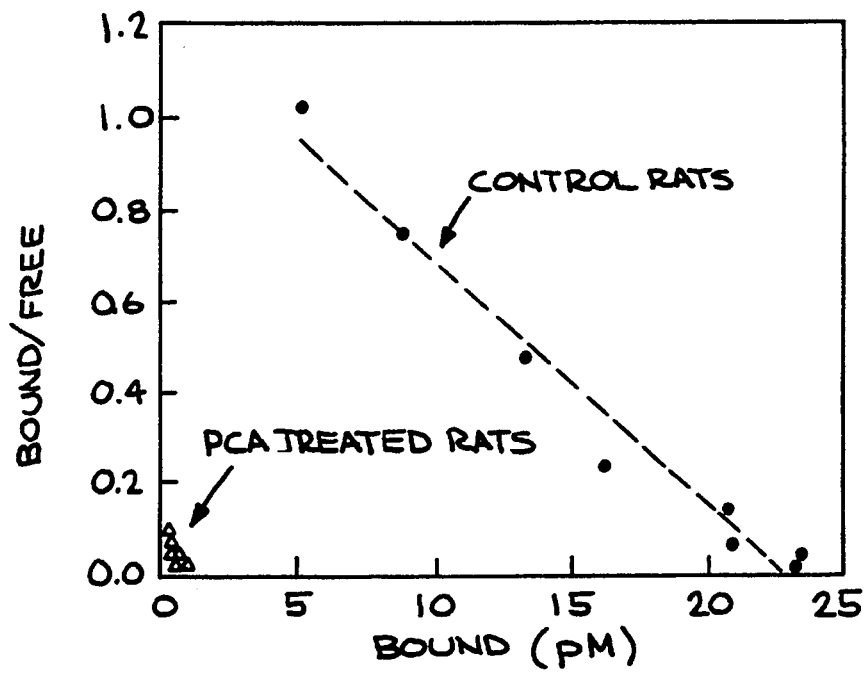
FIG. 1 is a Scatchard plot which shows the specificity of iodinated (5-iodo) 6 nitroquipazine (INQUIP) as compared to a control after rats have been treated with p-chloroamphetamine (PCA) which destroys the serotonergic system in the brain. The specificity of the INQUIP is shown by the enormous reduction in binding after PCA treatment without change in affinity.

The general synthetic route to the 3-, 5-, 7-, and 8-substituted-6-nitroquipazines of this invention involves the initial formation of the 3-, 5-, 7-, and 8-bromo-2-chloroquinolines followed by further elaboration of the 2 and 6 positions (for compounds 1, 2a, 3, and 4) or the 2, 5, and 6 positions (for compounds 2a–2e). All of the syntheses include a coupling at the 2 position with an N-protected piperazine and a nitration at the 6 position.

Synthesis of Substrates

3-Bromoquinoline N-oxide (6). To a solution of 3-Bromoquinoline 5 (2.08 g, 10 mmol) in CHCl$_3$ (5 ml) was added CH$_3$CO$_2$OH (5 ml, 32% solution in dilute HOAc, 20 mmol) and the mixture was stirred overnight. Acetone (3 ml) was added and the mixture was stirred an additional 15 min then poured into saturated NaHCO$_3$ (aq) and extracted with CH$_2$Cl$_2$. The combined extracts were dried (K$_2$CO$_3$) and concentrated to yield pure 6 (2.26 g, 100%) as a tan solid. $^1$H NMR d (d=delta) (ppm): 7.7 dd (CH atom), 7.8 m (2 CH atom), 7.9 s (CH atom), 8.6 s (CH atom), 8.7 d (CH atom).

3-Bromo-2-chloroquinoline (7). To POCl$_3$ (7.5 ml, 80 mmol) was added in portions solid 6 (2.25 g, 10 mmol). The mixture was stirred at room temperature for 30 min and then 60° C. for 10 min. The mixture was then poured into cold 1M NaOH extracted with CH$_2$C$_2$. The combined extracts were dried (K$_2$CO$_3$) and concentrated to a residue which was purified by flash chromatography (EtOAc) to afford 3-Bromo-2-chloroquinoline 7 (1.95 g, 80%). $^1$H NMR d (ppm): 7.6 dd ( CH atom), 7.7 m (2 CH atom), 8.0 d (CH atom), 8.5 s (CH arom)

3-Bromo-6-nitro-2-piperazinylquinoline (1). A stirred mixture of 7 (200 mg, 0.83 mmol) and 1-Piperazinecarboxaldehyde (4 ml) was heated at 120° C. for 15 min. under argon. The mixture was then cooled and diluted with 0.5M NaHCO$_3$. The aqueous phase was extracted with ether (3×) and the combined extractions were dried (MgSO$_4$). Concentration yielded a residue which was immediately dissolved in THF (10 ml) and 4M H$_2$SO$_4$ (5 ml). The solution was then brought to reflux and stirred for 1 h. The solution was cooled and poured into 1M NaOH. The resulting suspension was then extracted twice with ether and the ether extracts were dried (MgSO$_4$). Evaporation of the solvent afforded a material which was immediately dissolved in H$_2$SO$_4$ (5 ml). To this solution was added dropwise HNO$_3$ (0.1 ml) at −10° C. The mixture was stirred 15 min. at −10° -0° C., poured onto ice, and diluted with 1M NaOH until basic. The mixture was then extracted with CH$_2$C$_2$ (3×), and the combined organic layers were dried (MgSO$_4$). Concentration yielded the quipazine analogue 1 (189 mg, 68% based on 7). $^1$H NMR d (ppm): 1.9 br (NH), 3.1 dd (CH$_2$), 3.5 dd (CH$_2$), 7.8 d (CH arom), 8.3 s (CH arom), 8.3 d (CH arom), 8.5 s (CH arom).

5-Bromo-2-chloroquinoline (9). To a solution of 2-Chloroquinoline (8) (1.0 g, 6.11 mmol) in 1:1 H$_2$SO$_4$: H$_2$O (30 ml) was added N-Bromosuccinimide (1.7 g, 9.55 mmol). The mixture was stirred at 35° C. for 38 h and then cooled. The solution was diluted with enough 50% NaOH (aq) to maintain pH<1 and the mixture was extracted with CH$_2$Cl$_2$. The combined organic layers were washed with sat. NaHCO$_3$ (aq) and dried (MgSO$_4$). Concentration of the solvent afforded a dark brown oil (0.078 g, 79%) which was sequentially purified by flash chromatography (85:15 Hexane:CH$_2$Cl$_2$) and MPLC (85:15 Hexane:CH$_2$Cl$_2$) to afford 9 (0.22 g, 15%) as a white amorphous solid (m.p. 71° -72° C.). $^1$H NMR d (ppm): 7.39 d (CH arom), 7.51 dd (CH arom), 7.74 d (CH arom), 7.91 d (CH atom), 8.37 d (CH arom).

5-Bromo-2-piperazinylquinoline (10). A stirred mixture of 9 (342 mg, 1.41 mmol) and 1-Piperazinecarboxaldehyde (4 ml) was heated at 125° C. for 30 min. under argon. The mixture was then cooled and diluted with saturated aqueous NaHCO$_3$. The aqueous phase was extracted with ether (3×) and the combined extractions were dried (MgSO$_4$). Concentration yielded a solid (400 mg) which was immediately dissolved in THF (10 ml) and 4M $H_2SO_4$ (5 ml). The solution was then brought to reflux and stirred for 1 h. The solution was cooled and poured into 1M NaOH. The resulting suspension was then extracted twice with ether and the ether extracts were dried ($MgSO_4$). Evaporation of the solvent afforded 10 (300 mg, 82%) as a white solid (m.p. 94° –96° C.) sufficiently pure for the next step. $^1$H NMR d (ppm): 1.81 s (NH), 2.96 dd ($CH_2$), 3.67 dd ($CH_2$), 6.97 d (CH arom), 7.32 dd (CH atom), 7.42 d (CH arom), 7.60 d (CH arom), 8.19 d (CH arom).

5-Bromo-6-nitro-2-piperazinylquinoline (2a). To a −10° C. solution of 10 (300 mg, 1.03 mmol) in $H_2SO_4$ (10 ml) was added dropwise $HNO_3$ (0.25 ml). The mixture was stirred 15 min. at −10° –0° C., poured onto ice, and diluted with 1M NaOH until basic. The mixture was then extracted with $CH_2Cl_2$ (3×), and the combined organic layers were dried ($MgSO_4$). Concentration yielded 2a (240 mg, 70%) as a yellowish solid which was utilized in the next step without further purification. (m.p.>230° C., dec. ). $^1$H NMR d (ppm): 1.79 s (NH), 3.00 dd ($CH_2$), 3.80 dd ($CH_2$), 7.07 d (CH arom), 7.57 d (CH arom), 7.81 d (CH arom), 8.37 d (CH arom).

5-Vinyl-2-chloroquinoline (11 ). A mixture of 5-Bromo-2-chloroquinoline (9) (155 mg, 0.64 mmol), vinyltributyltin (230 mg, 0.73 mmol), and Pd(PPh$_3$)$_4$ (15 mg, 2 mol %) in toluene (10 ml) was refluxed under an argon atmosphere for 3 h. The mixture was cooled and the solvent was evaporated. The resulting residue was subjected to HPLC purification (Whatman Partisil 10 column, 95: 5 $CH_2Cl_2$: EtOAc) to afford the vinyl derivative 11 (70 mg, 58%). $^1$H NMR d (ppm): 5.52 dd (CH vinyl), 5.79 dd (CH vinyl), 7.28 dd (CH vinyl), 7.36 d (CH arom), 7.64 dd (CH arom), 7.68 d (CH arom), 7.93 dd (CH arom), 8.34 d (CH arom).

5-(2-Hydroxyethyl)-2-chloroquinoline (12). To a 0° C. solution of 11 (70 mg, 0.37 mmol) in dry THF (5 ml) was added 9-BBN (1.5 ml, 0.5M solution in THF, 0.75 mmol) and the solution was stirred overnight at room temperature. The organoborane was oxidized by adding 1M NaOH (aq) (0.5 ml) and 30% $H_2O_2$ (0.5 ml) and then the mixture was poured into water and extracted with ether. The ether extracts were dried ($MgSO_4$) and concentrated to afford the alcohol 12 (70 mg, 91%) which was sufficiently pure for the next step. $^1$H NMR d (ppm): 3.30 t ($CH_2$), 3.95 t ($CH_2$), 7.35 d (CH arom), 7.40 d (CH arom), 7.60 dd (CH arom), 7.75 d (CH arom), 8.35 d (CH arom).

5-(2-Hydroxyethyl)-2-(1-tert-butylcarboxypiperazinyl)quinoline (13). A mixture of 12 (70 mg, 0.34 mmol) and tert-Butyl-1-piperazinecarboxylate (4 g) was heated at 120° C. for 4 h under an argon atmosphere. The mixture was cooled and diluted with saturated $NaHCO_3$ (aq). The mixture was then extracted twice with ether, and the combined ether extracts were dried ($MgSO_4$). Evaporation of the solvent afforded a residue which was subjected to HPLC purification (Whatman Partisil 10 column, EtOAc). Concentration of the appropriate fractions yielded the carbamate 13 (50 mg, 42%). $^1$H NMR d (ppm): 1.48 s (3 $CH_3$), 3.20 t ($CH_2$), 3.55 m ($NCH_2$), 3.71 m ($NCH_2$), 3.91 t ($CH_2$), 6.96 d (CH arom), 7.11 d (CH arom), 7.45 dd (CH arom), 7.60 d (CH arom), 14 d (CH arom).

5-(2-Fluoroethyl)-2-(1-tert-butylcarboxypiperazinyl)quinoline (14). To a −78° C. solution of Diethylaminosulfur trifluoride (DAST) (0.06 ml, 0.42 mmol) in dry $CH_2C_2$ was slowly added a solution of 13 (50 mg, 0.14 mmol) in dry $CH_2C_2$ (3 ml). The solution was allowed to warm to room temperature and stirred for 1 h. Saturated aqueous $NaHCO_3$ was added and the mixture was extracted with $CH_2Cl_2$. The organic phase was dried ($MgSO_4$) and concentrated. The residue was purified by HPLC (Whatman Partisil M9 column, 90:10 $CH_2Cl_2$:EtOAc) to afford the fluoroethyl derivative 14 (33 mg, 66%). $^1$H NMR d (ppm): 1.48 s (3 $CH_3$), 3.36 dt ($CH_2$), 3.56 dd ($NCH_2$), 3.71 dd ($NCH_2$), 4.69 dt ($CH_2$), 6.99 d (CH arom), 7.11 d (CH arom), 7.46 dd (CH arom), 7.61 d (CH arom), 8.10 d (CH arom).

5-(2-Fluoroethyl)-6-nitro-2-piperazinylquinoline (2b). To a −10° C. solution of 14 (30 mg, 0.084 mmol) in $H_2SO_4$ (2 ml) was added dropwise $HNO_3$ (0.1 ml). The mixture was stirred 10 min. at −10° C., poured onto ice, and diluted with saturated $NaHCO_3$ (aq) until basic. The mixture was then extracted with $CH_2Cl_2$ (3×), and the combined organic layers were dried ($MgSO_4$). Concentration yielded a residue which was purified by reverse phase HPLC (Whatman Partisil 10 ODS-3 column, MeOH). Concentration of the appropriate fractions afforded the quipazine derivative 2b (11 mg, 44%). $^1$H NMR d (ppm): 1.90 br s (NH), 3.02 dd ($NCH_2$), 3.62 dt ($CH_2$ ), 3.82 dd ($NCH_2$), 4.86 dt ($CH_2$), 7.08 d (CH arom), 7.60 d (CH arom), 8.07 d (CH arom), 8.30 d (CH arom).

5-Bromo-6-nitro-2-(1-tert-butylcarboxypiperazinyl)quinoline (15). To a solution of 2a (243 mg, 0.72 mmol) in dioxane (15 ml) and water (10 ml) was added Et$_3$N (0.19 ml, 1.36 mmol) and BOC-ON (Aldrich, 208 mg, 0.84 mmol). The mixture was stirred at room temperature for 1.5 h and then poured into water. The mixture was extracted with ether and the combined ether extracts were washed with water and dried (MgSO4). The ether extracts were combined, dried ($MgSO_4$), and concentrated. The residue was purified by HPLC (Whatman Partisil 10 column, 90:10 $CH_2Cl_2$:EtOAc) to afford the carbamate 15 (230 mg, 73%) (m.p. 179° –180° C.). $^1$H NMR d (ppm): 1.49 s (3 $CH_3$), 3.59 dd ($CH_2$), 3.83 dd ($CH_2$), 7.09 d (CH arom), 7.61 d (CH arom), 7.93 d (CH arom), 8.42 d (CH arom).

5-Tributylstannyl-6-nitro-2-(1-tert-butylcarboxypiperazinyl)quinoline (16). To a −100° C. solution of 15 (200 mg, 0.46 mmol) in dry THF (8 ml) was added nBuLi (1.6M, 0.50 mmol, 0.31 ml) dropwise. The resulting black-green solution was stirred for 10 min. at which time Bu$_3$SnCl (0.15 ml, 0.54 mmol) was added neat. The solution was allowed to reach room temperature and stirred 2 h. Water was added and the mixture was extracted with ether. The combined ether extracts were dried ($MgSO_4$) and concentrated to a brown oil. HPLC purification of the oil (Whatman Partisil 10 column, 90:10 $CH_2Cl_2$:EtOAc) afforded the tributylstannyl derivative 16 (150 mg, 50%). $^1$H NMR d (ppm): 0.85 t ($CH_3$), 1.15–1.55 m (3 $CH_2$), 1.49 s (3 $CH_3$), 3.58 dd ($CH_2$), 3.83 dd ($CH_2$), 7.00 d (CH arom), 7.63 d (CH arom), 8.18 d (CH arom), 8.30 d (CH arom).

5-Iodo-6-nitro-2-piperazinylquinoline (2c). To a solution of 16 (70 mg, 0.11 mmol), 1.0M NaI (aq) (0.22 ml, 0.22 mmol), and 1M $H_3PO_4$ (0.1 ml) in EtOH (5 ml) was added Dichloramine T (26 mg, 0.11 mmol). The resulting brown solution was stirred for 20 min. at room temperature at which time a precipitate formed. The mixture was diluted with 10% $Na_2S_2O_3$ (aq) and then extracted with ether. The combined ether extracts were dried ($MgSO_4$) and concentrated to a residue which was immediately dissolved in THF (5 ml) and 4M $H_2SO_4$ (5 ml). The solution was refluxed for 1 h, cooled to room temperature, and made basic with 1M NaOH. The mixture was extracted with $CH_2Cl_2$, and the organic phase was dried ($MgSO_4$) and concentrated to afford 2c (21 mg, 50%). $^1H$ NMR d (ppm): 1.70 br s (NH), 3.00 dd ($CH_2$), 3.80 dd ($CH_2$), 7.02 d (CH arom), 7.60 d (CH arom), 7.86 d (CH arom), 8.32 d (CH arom).

[$^{125}I$]5-Iodo-6-nitro-2-piperazinylquinoline (2d). This compound was prepared following a procedure similar to that described above for 2 c except that $Na^{125}I$ was used instead of NaI. After cleavage of the BOC group the yield of 2 d was 65%.

5-Fluoro-6-nitro-2-piperazinylquinoline (2 e). To a solution of 15 (80 mg, 0.18 mmol) in DMSO (4 ml) was added KF (32 mg, 0.54 mmol). The mixture was heated under argon at 120° C. for 5.5 h. The mixture was then cooled, diluted with water, and extracted with ether. The combined ether extractions were dried ($MgSO_4$) and concentrated. The residue was passed through a short silica gel plug (90:10 $CH_2Cl_2$:EtOAc) and the solvent evaporated to furnish a material which was immediately dissolved in THF (5 ml) and 4M $H_2SO_4$ (5 ml). The solution was then brought to reflux and stirred for 1 h. The solution was cooled and poured into 1M NaOH. The resulting suspension was then extracted with ether and the ether extracts were dried ($MgSO_4$). Evaporation of the solvent afforded 2 e (30 mg, 60%). $^1H$ NMR d (ppm): 1.79 s (NH), 3.00 dd ($CH_2$), 3.80 dd ($CH_2$), 7.09 d (CH arom), 7.48 d (CH arom), 8.18 dd (CH arom), 8.33 d (CH arom).

7-Trimethylstannylquinoline (18). To a 0° C. solution of 7-Hydroxyquinoline 17 (2.0 g, 13.8 mmol) in pyridine (10 ml) was slowly added trifluoromethanesulfonic anhydride (2.5 ml, 15 mmol). The solution was stirred 5 min. at 0° C. and 3 h at room temperature. The solution was then poured into 1M HCl and the mixture was extracted with ether (3×). The combined ether extracts were dried ($MgSO_4$) and concentrated. The residue was taken up in $CH_2Cl_2$ and passed through a short silica gel pad. The appropriate fractions were concentrated to afford the triflate as a yellow solid (2.03 g, mmol) which was immediately diluted with dioxane (50 ml). To this solution were added $Pd(PPh_3)_4$ (108 mg, 2 mol %), $(Me_3Sn)_2$ (2.3 g, 7.0 mmol), and LiCl (598 mg, 14.1 mmol). The mixture was refluxed for 6 h, cooled, and poured into water. The mixture was then extracted with ether, and the combined ether extracts were dried ($MgSO_4$) and concentrated. The residue was taken up in $CHCl_3$ and passed through a short silica gel pad with $CHCl_3$ and 90:10 $CHCl_3$:EtOAc as successive eluents. The appropriate fractions were concentrated to afford the trimethyltin derivative 18 (1.4 g, 34% from 17). $^1H$ NMR d (ppm): 0.36 s (3 $CH_3$), 7.35 dd (CH arom), 7.63 d (CH arom), 7.75 d (CH arom), 8.10 d (CH arom), 8.24 dd (CH arom), 8.88 dd (CH arom).

7-Bromo-2-chloroquinoline (19). To a −78° C. solution of 18 (890 mg, 3.0 mmol) in dry THF (20 ml) was slowly added MeLi/LiBr (1.5M in ether, 2.2 ml, 3.3 mmol). The solution was stirred 30 min. at −78° C. at which time $Br_2$ (excess) was added dropwise. The solution was warmed to room temperature, quenched with water, and the mixture extracted with ether. The combined ether extracts were dried ($MgSO_4$) and concentrated. The residue was taken up in $CH_2Cl_2$ and passed through a short silica gel pad. The appropriate fractions were concentrated to afford a material which was immediately diluted with $CHCl_3$ (20 ml). To this solution was added excess $CH_3CO_2OH$ (32% solution in dilute HOAc) and the mixture was stirred overnight. The mixture was then poured into saturated $NaHCO_3$ (aq) and extracted with ether. The combined ether extracts were dried ($MgSO_4$) and concentrated to a tan solid to which was added excess $POCl_3$ at 0° C. The mixture was warmed to 60° C., stirred for 15 min., and then cooled to room temperature. 1M NaOH was added and the mixture was extracted with ether. The combined ether extracts were dried ($MgSO_4$) and concentrated to a residue which was purified by HPLC (Whatman Partisil 10 column, 90:10 $CHCl_3$:EtOAc) to afford 7-Bromo-2-chloroquinoline 19 (70 mg, 10% from 18). $^1H$ NMR d (ppm): 7.4 d (CH arom), 7.7 s (2 CH arom), 8.2 d (CH arom), 8.3 s (CH arom).

7-Bromo-6-nitro-2-piperazinylquinoline (3). A stirred mixture of 19 (70 mg, 0.29 mmol) and 1-Piperazinecarboxaldehyde (4 ml) was heated at 125° C. for 30 min. under argon. The mixture was then cooled and diluted with saturated aqueous $NaHCO_3$. The aqueous phase was extracted with ether (3×) and the combined extractions were dried ($MgSO_4$). Concentration yielded a residue which was immediately dissolved in THF (10 ml) and 4M $H_2SO_4$ (5 ml). The solution was then brought to reflux and stirred for 1 h. The solution was cooled and poured into 1M NaOH. The resulting suspension was then extracted twice with ether and the ether extracts were dried ($MgSO_4$). Evaporation of the solvent afforded a material which was immediately dissolved in $H_2SO_4$ (5 ml). To this solution was added dropwise $HNO_3$ (0.1 ml) at −10° C. The mixture was stirred 15 min. at −10° -0° C., poured onto ice, and diluted with 1M NaOH until basic. The mixture was then extracted with $CH_2Cl_2$ (3×), and the combined organic layers were dried ($MgSO_4$). Concentration yielded the quipazine analogue 3 (47 mg, 48% from 19). $^1H$ NMR d (ppm): 1.60 s (NH), 3.00 dd ($CH_2$), 3.80 dd ($CH_2$), 7.04 d (CH arom), 7.87 d (CH arom), 7.95 s (CH arom), 8.24 s (CH arom).

8-Bromo-6-nitro-2-piperazinylquinoline (4). This compound can be prepared in the same manner as described above for 2a (see also Scheme II.A.) except that 8-Bromo-2-chloroquinoline 20 is utilized instead of the 5-bromo isomer 9, both of which are produced in the reaction of NBS with 2-Chloroquinoline 8. $^1H$ NMR d (ppm): 1.71 br (NH), 2.98 dd ($CH_2$), 3.84 dd ($CH_2$), 7.00 d (CH arom), 7.89 d (CH arom), 8.42 s (CH arom), 8.60 s (CH arom).

3-, 5-, 7-, and 8-Substituted-6-Nitroquipazines

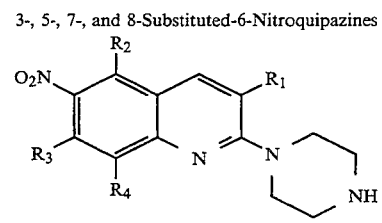

1. $R_2 = R_3 = R_4 = H, R_1 = Br$
2a. $R_1 = R_3 = R_4 = H, R_2 = Br$
2b. $R_1 = R_3 = R_4 = H, R_2 = CH_2CH_2F$
2c. $R_1 = R_3 = R_4 = H, R_2 = I$
2d. $R_1 = R_3 = R_4 = H, R_2 = {}^{125}I$
2e. $R_1 = R_3 = R_4 = H, R_2 = F$
3. $R_1 = R_2 = R_4 = H, R_3 = Br$
4. $R_1 = R_2 = R_3 = H, R_4 = Br$

Scheme I.
Synthesis of 3-Bromo-6-Nitroquipazine
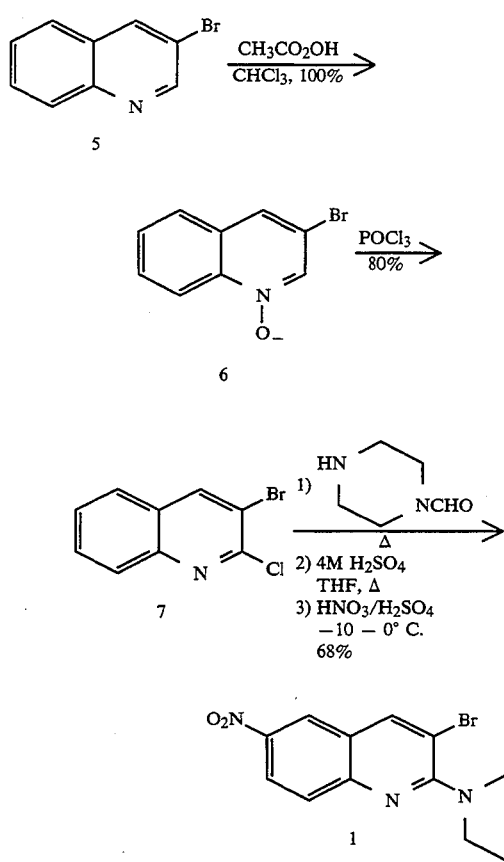
Scheme II.
Synthesis of 5-Substituted-6-Nitroquipazines
A. 5-Bromo
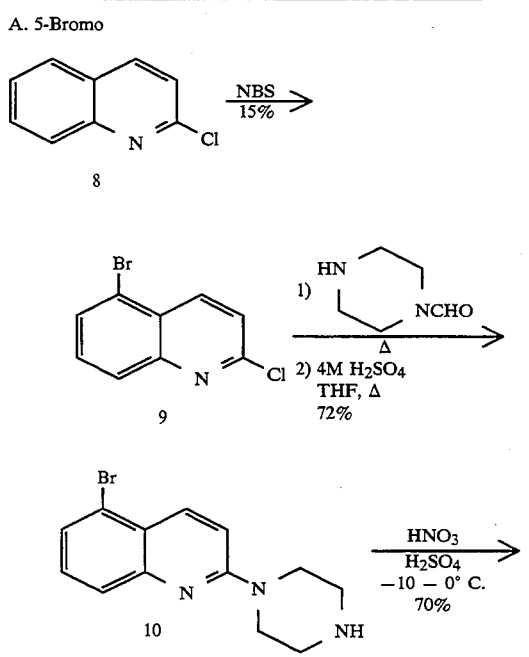
Scheme II.
Synthesis of 5-Substituted-6-Nitroquipazines
B. 5-Fluoroethyl
C. 5-Iodo
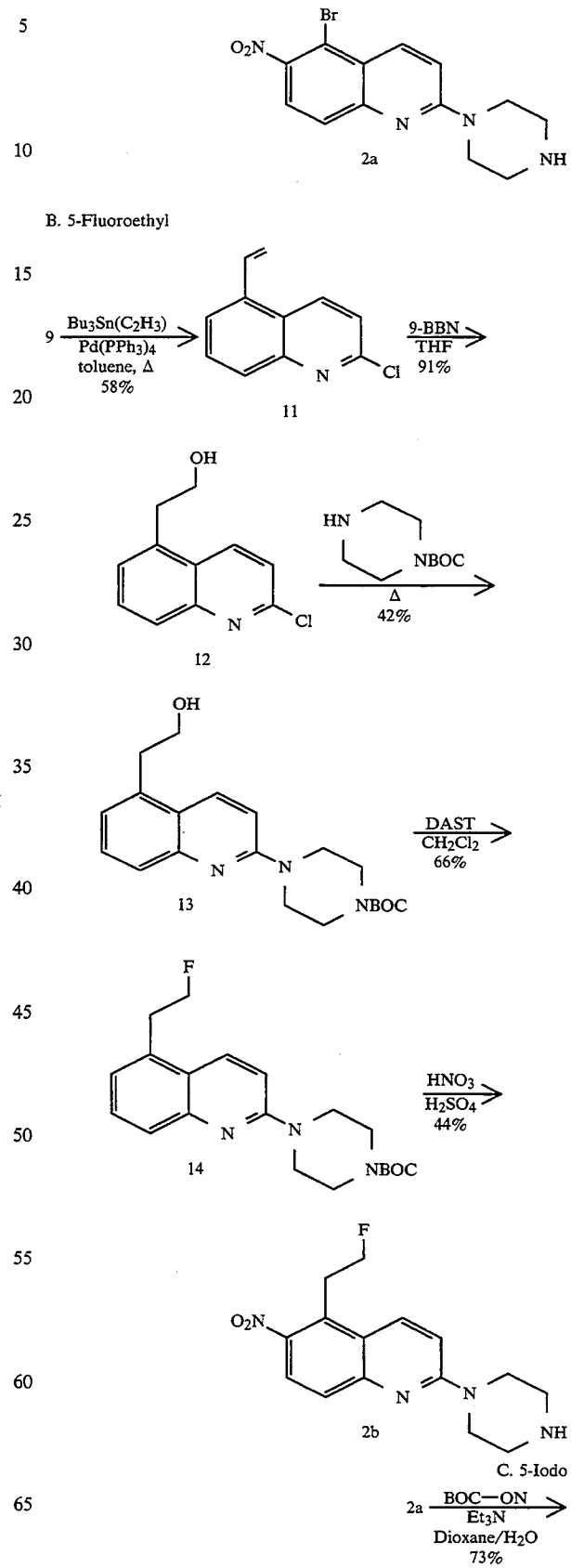

-continued
Scheme II.
Synthesis of 5-Substituted-6-Nitroquipazines

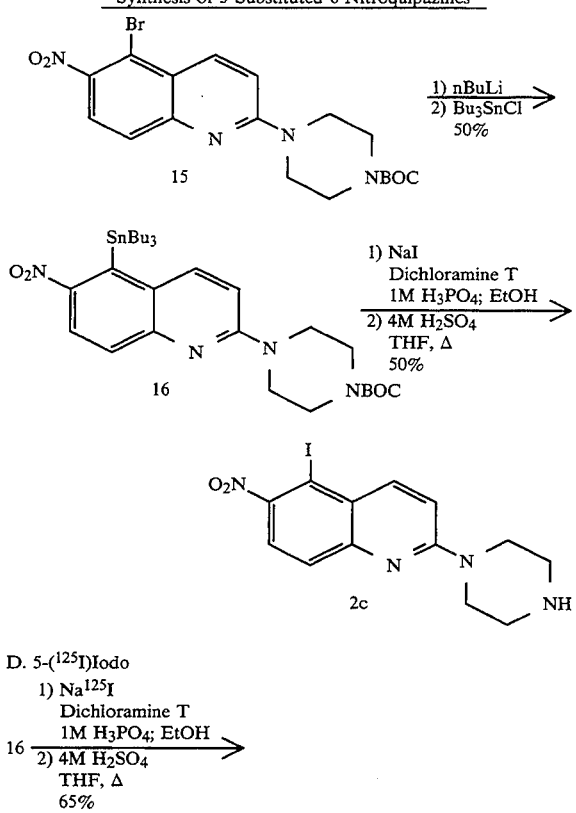

D. 5-($^{125}$I)Iodo

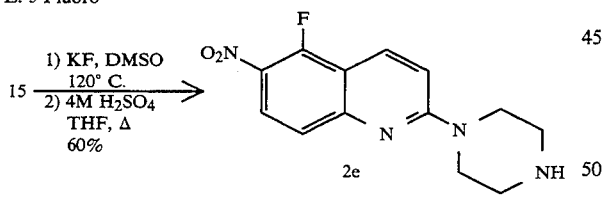

E. 5-Fluoro

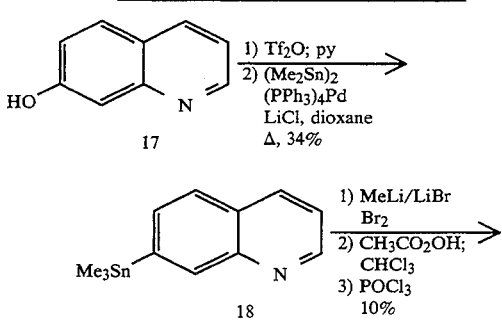

Scheme III.
Synthesis of 7-Bromo-6-Nitorquipazine

-continued
Scheme III.
Synthesis of 7-Bromo-6-Nitorquipazine

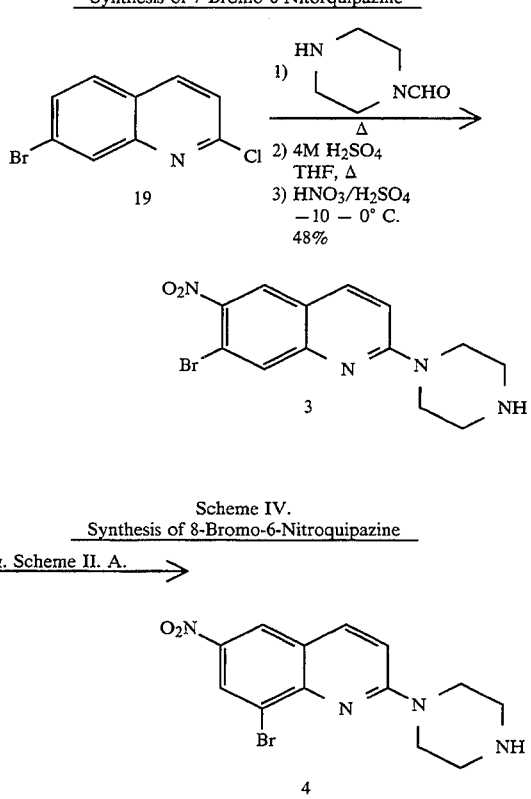

Scheme IV.
Synthesis of 8-Bromo-6-Nitroquipazine

8 $\xrightarrow{\text{e.g. Scheme II. A.}}$

In order to carry out measurement of serotonin uptake sites according to this invention, conventional methods can be followed except that a radiolabeled nitroquipazine of this invention is used as the radioligand. In other words, according to the method of this invention, a sample is allowed to react (incubation) with the radioligand of the invention, then the radioactivity of the radioligand bound to the sample is measured.

Samples may be various tissues and cell membranes of animals including human. Examples are tissues of brain, intestine and blood vessel and platelets. Incubation is carried out in a suitable buffer at 0° to 37° C. for 5 minutes to several hours. The radioactivity of the radioligand bound to the sample is measured by a scintillation counter after unreacted ligand is removed.

In vitro Studies of 5-$^{125}$I-6-NQP

The binding characteristics of the 5-$^{125}$I-6-NQP were determined by incubating varying concentrations of the radioligand with isolated rat brain membrane preparations, and the data were analyzed via a Scatchard plot to determine the affinity of the ligand (Kd) for the receptor (FIG. 1).

The specificity of the 5-$^{125}$I-6-NQP for the serotonergic system was determined by two separate sets of experiments: in the first, rats were treated with p-chloroamphetamine (PCA) to lesion the serotonergic system and thus reduce the concentration of serotonin uptake sites available for binding to the ligand. In vitro assays were performed with extracts made from brains isolated from PCA-treated and control rats, and a reduction in the total 5$^{125}$I-6-NQP binding (Bmax) was observed in the PCA-treated animals (FIG. 1), with little change in the affinity (Kd), indicating that the 5-$^{125}$I-6-NQP binds to a serotonergic receptor/ or uptake protein.

Figure 2:
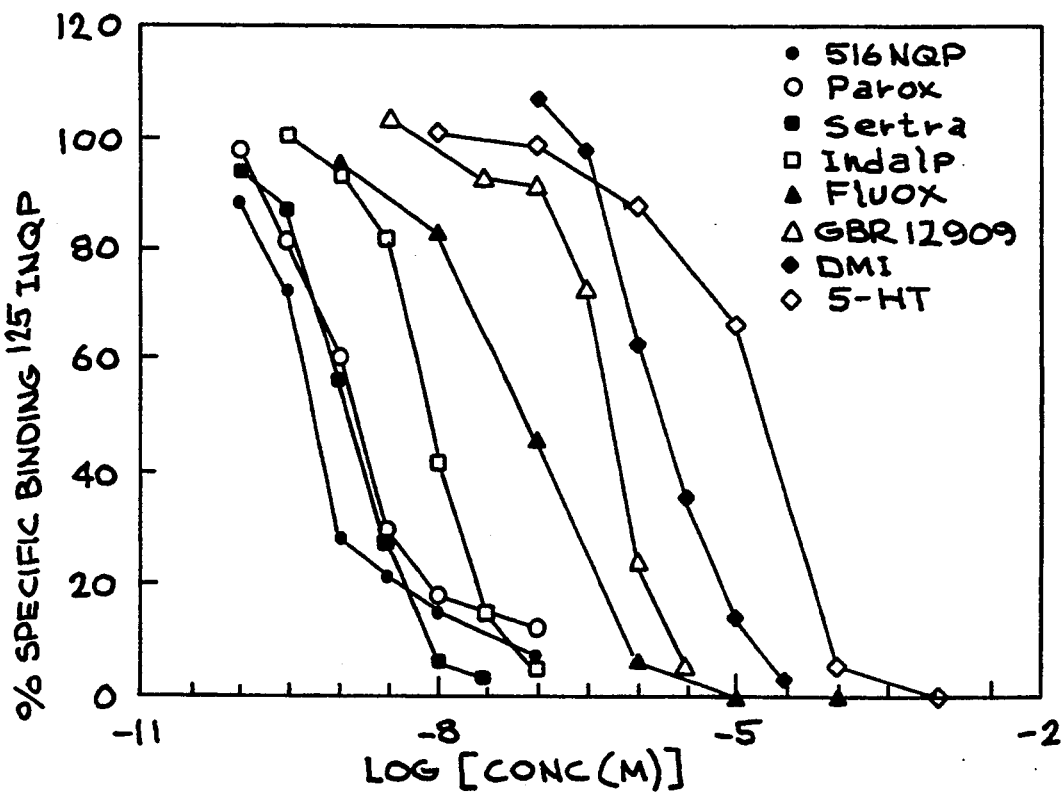
FIG. 2 is a graph illustrating the inhibition curves of various serotonin uptake inhibitors compared to iodinated 6-nitroquipazine.

In the second set of experiments, competition experiments were performed with known agonist and antagonists to the serotonin uptake system, post synaptic serotonin receptors, and a receptors of other brain receptor systems. These compounds were incubated against 5-$^{125}$I-6-NQP to determine the concentration needed to displace 5-$^{125}$I-6-NQP from the membrane preparations. The strongest competitors were those specific for the serotonin uptake system, (FIG. 2). Little competitive activity was observed in assays with non-serotonergic ligands included. These data from the competition experiments illustrate the specificity of the 5-$^{125}$I-6NQP for the serotonin uptake system, and also indicate that the relative potency of the ligand for the uptake site is greater than that observed for other serotonin uptake ligands (e.g. sertraline [Zoloft] and fluoxetine [Prozac]).

In vitro binding results of 6-NQP analogues

The relative potencies of brominated analogues of 6-nitroquipazine were determined by competition studies for the 5-HT (serotonin) reuptake complex with 3H-paroxetine. Rat cortical brain homogenates were incubated with 3H-paroxetine and with varying amounts of the brominated analogues, and in vitro inhibition constants (Ki) were determined by measuring the displacement of the radiolabeled paroxetine from the binding site. A potency ratio was also determined by comparing the Ki of the analogue to the Ki experimentally determined for the unsubstituted 6-Nitroquipazine. The results are provided in Table 1.

The data indicate that substitutions on the 3, 5, 7 and 8 positions have potential uses as imaging agents and may also have clinical uses. The affinity of the compound substituted in the 4 position is too low to be of any use. As a comparison, the anti-depressant drug Prozac has a potency ratio in the range of 80.

TABLE 1

| In vitro Inhibition Constants (Ki) of the 6-Nitroquipazine Derivatives for the 5-HT Reuptake Site | | |
|---|---|---|
| Compound | Ki (nM) | Potency Ratio |
| 6-NQP | 0.23 ± 0.06 | 1 |
| 3-Br-6-NQP | 9.6 ± 2.6 | 42 |
| 4-Br-6-NQP | 200 ± 80 | 870 |
| 5-Br-6-NQP | 0.13 ± 0.02 | 0.57 |
| 7-Br-6-NQP | 4.1 ± 1.5 | 18 |
| 8-Br-6-NQP | 18 ± 3 | 78 |

The radioligand used in this invention is more potent than those which have been used widely. Therefore, the nitroquipazines of this invention are suitable radioligands for studying the serotonin uptake sites in brains and platelets from patients with depression or other psychiatric and non-psychiatric illness which involve the serotonin system.

In Vivo Studies of 5-$^{125}$I-6-NQP

Figure 3A:
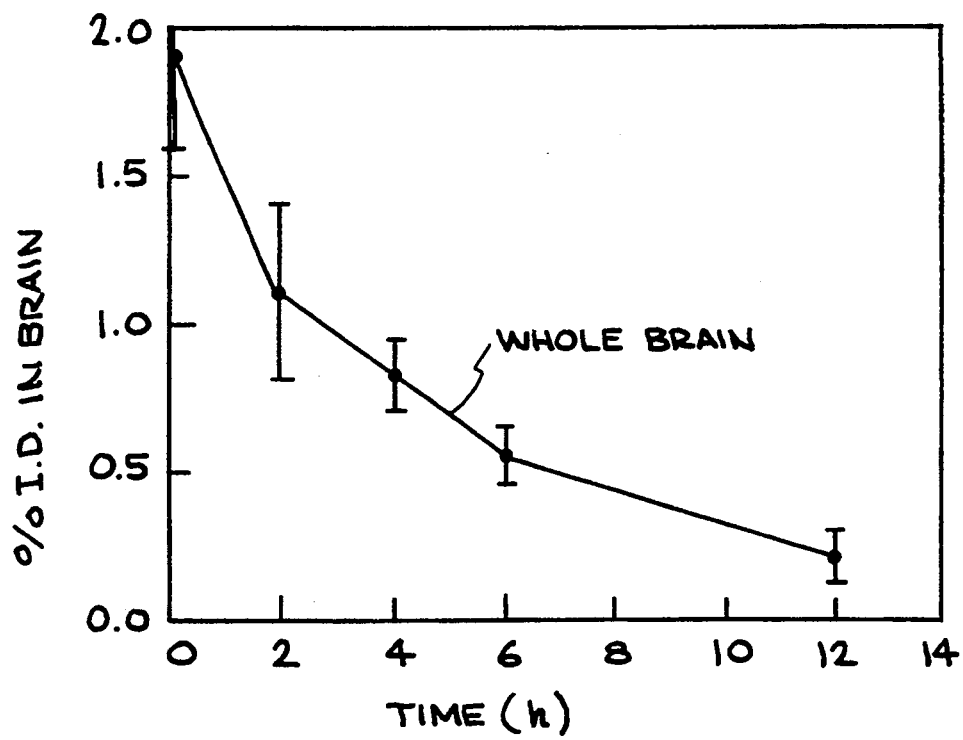
FIG. 3 (Left panel) Shows whole rat brain activity after i.v. injection of 5-$^{125}$I-6-NQP (average of 3–5 rats at each time point). (Right panel) Regional distribution of radioactivity in rat brain at different times after 5-$^{125}$I-6-NQP injection (3–5 rats per time point). Standard errors are not shown for clarity, but they average 10–20% of the values at each time point. PFC=prefrontal cortex; O.T.=olfactory tubercle; Hippo=hippocampus; Hypothal=hypothalamus; Cb=cerebellum.
Figure 3B:
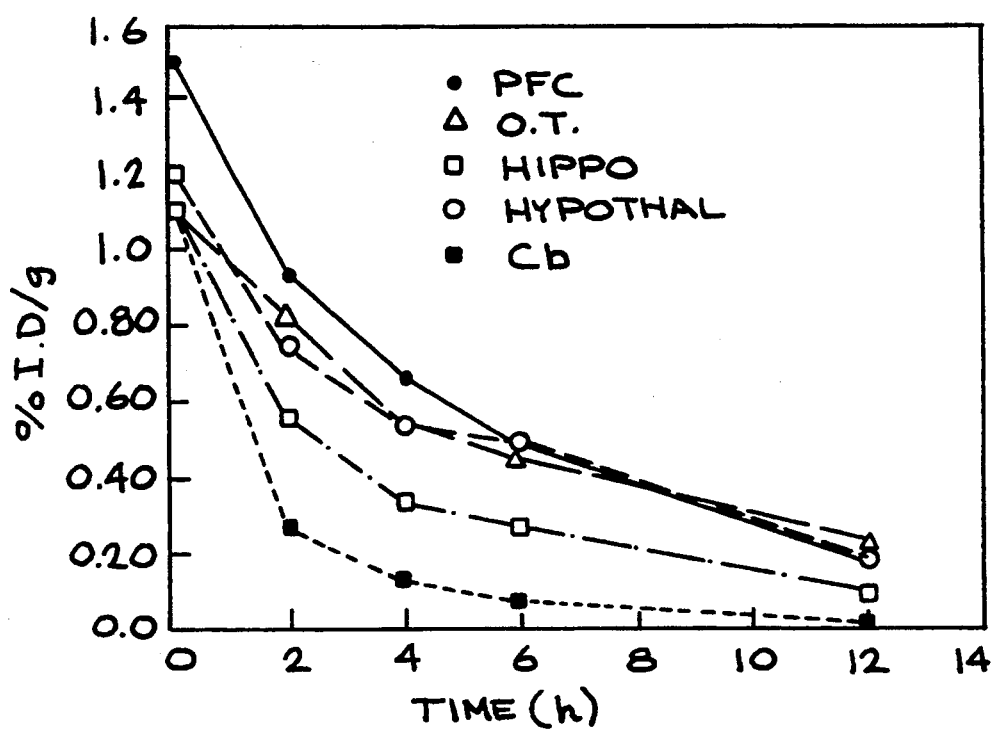

Whole body distribution studies were performed in rats in accordance with the method of Carl Mathis, et al described in Nuclear Medicine and Biology 19: 571–588 (1992). The whole brain uptake and clearance of 25 µCi (11 pmoles) of 5-$^{125}$I-6-NQP in rats out to 12 h post i.v. injection are shown in FIG. 3. It is clear that 5-$^{125}$I-6-NQP has good brain penetration since 1.9% of the injected dose (I.D.) accumulated in the whole brain at 5 min post injection. The data indicate a slow steady loss of activity from the brain over 12 h. The microdissection of various brain regions gave the regional activity data shown in FIG. 3 (right panel). These results agree with immunochemical findings of Steinbusch (1981) who reported that the hypothalamus, prefrontal cortex, and olfactory tubercle are rich in serotonergic projections, while the hippocampus contains fewer serotonergic projections, and the cerebellum is nearly devoid of presynaptic 5-HT sites.

Nonspecific and Specific Binding

Figure 4A:
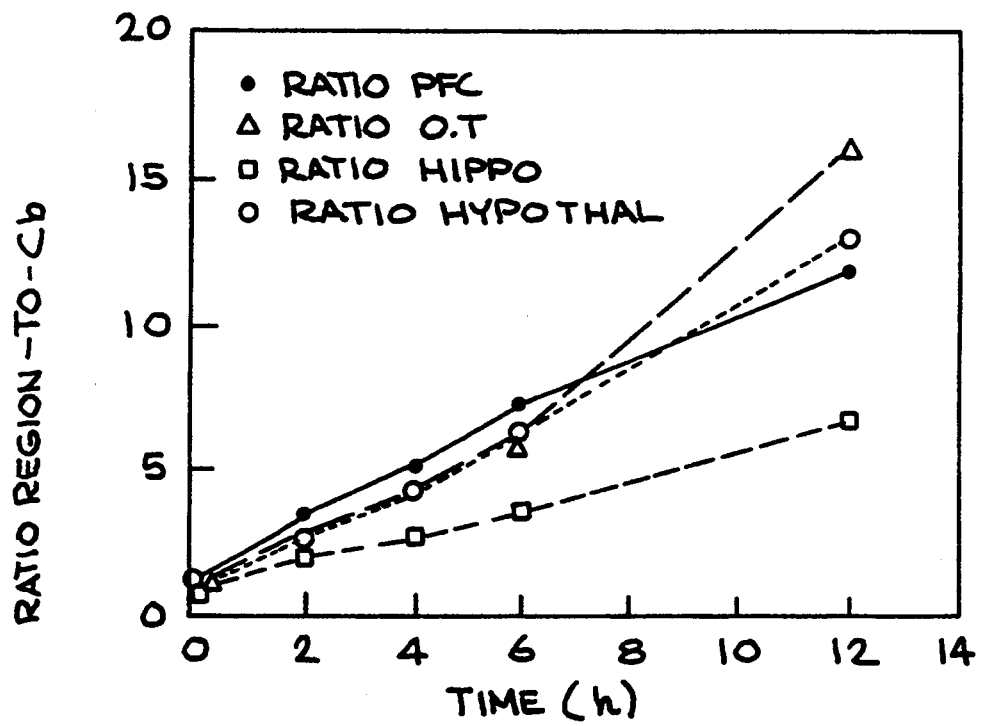
FIG. 4 (Left panel) Shows ratios of regional rat brain radioactivity concentrations to that in the cerebellum at time points ranging from 5 min to 12 h post injection 5-$^{125}$I-6-NQP. Abbreviations are the same as in FIG. 3. (Right panel) Time course of specific binding (total regional minus cerebellar concentrations) in the hypothalamus.
Figure 4B:
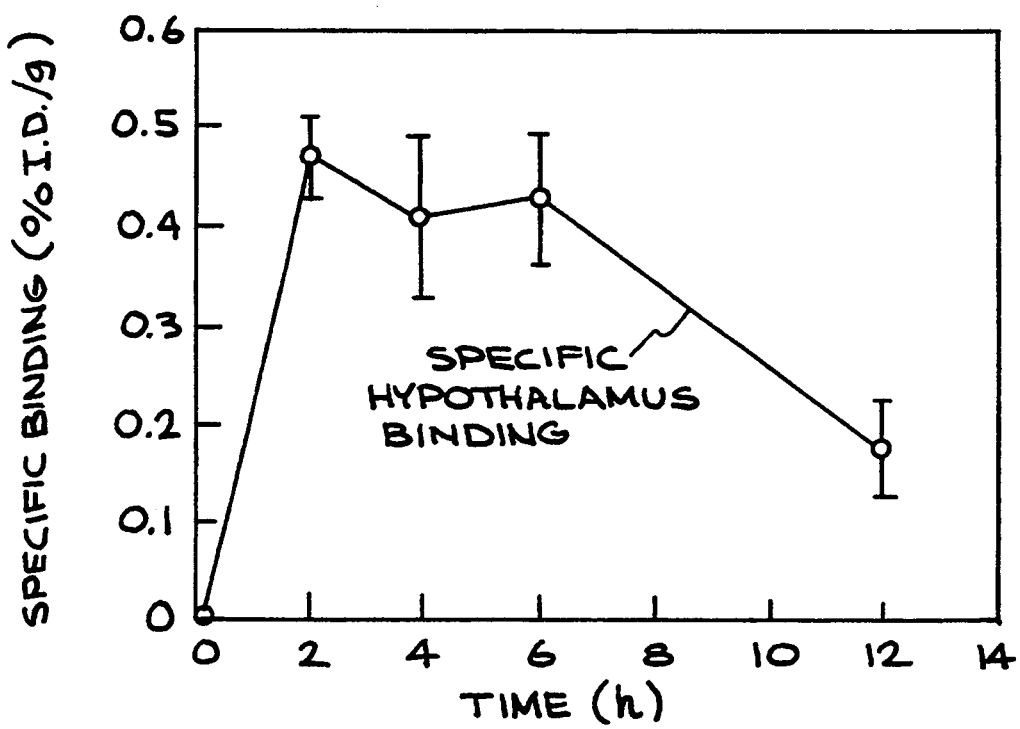

The clearance of nonspecific binding shown in FIG. 3 (as estimated from cerebellar activity concentrations) is more rapid than that of radioactivity clearance from brain regions containing high concentrations of 5-HT innervation. The ratios of regional activity concentrations to cerebellar concentrations are plotted in the left panel of FIG. 4. The ratios increase in a nearly linear manner over the 12 h period post injection. Also plotted in the right panel of FIG. 4 is the time course of specific binding (total regional radioactivity cerebellar radioactivity) in a representative tissue.

In Vivo Blocking Studies

A critical test of the in vivo behavior of the radioligand is the ability to block its specific binding. Several potent 5-HT uptake complex ligands have failed this test. The effects of the co-injection of blocking doses of paroxetine (2mg/kg) together with 5-$^{125}$I-6-NQP are shown in FIG. 5.

Figure 5:
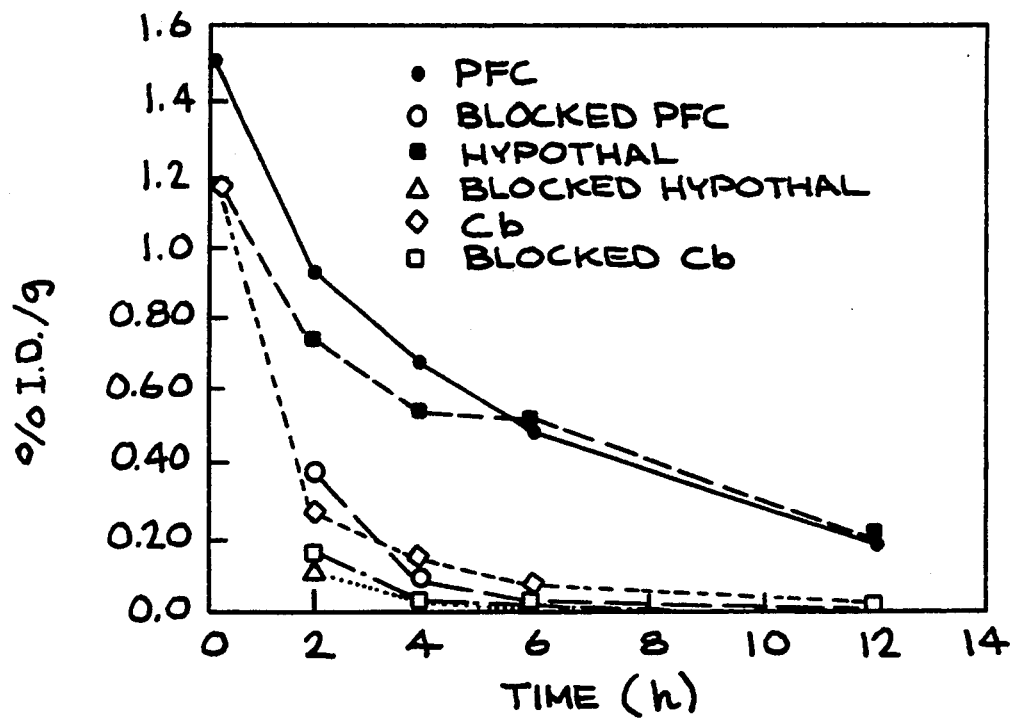
FIG. 5 Is a plot of activity concentration in various rat brain regions following the i.v. injection of 5-$^{125}$I-6-NQP in rats. The unblocked studies include a 5 min. time point which was not determined in the blocked studies. Blocking studies involved the i.v. tail vein co-injection of 2 mg/kg paroxetine with the 5-$^{125}$I-6-NQP. Abbreviations are as defined in FIG. 3.

As shown in FIG. 5, the co-injection of paroxetine resulted in a decrease in total binding in all rat brain regions measured; cerebellar radioactivity decreased only slightly, while prefrontal cortex and hypothalamus radioactivity was greatly diminished in the blocked state. All blocked brain tissue radioactivity concentrations (as well as that of unblocked cerebellum) were approximately equal at 4 h post injection.

Figure 6:
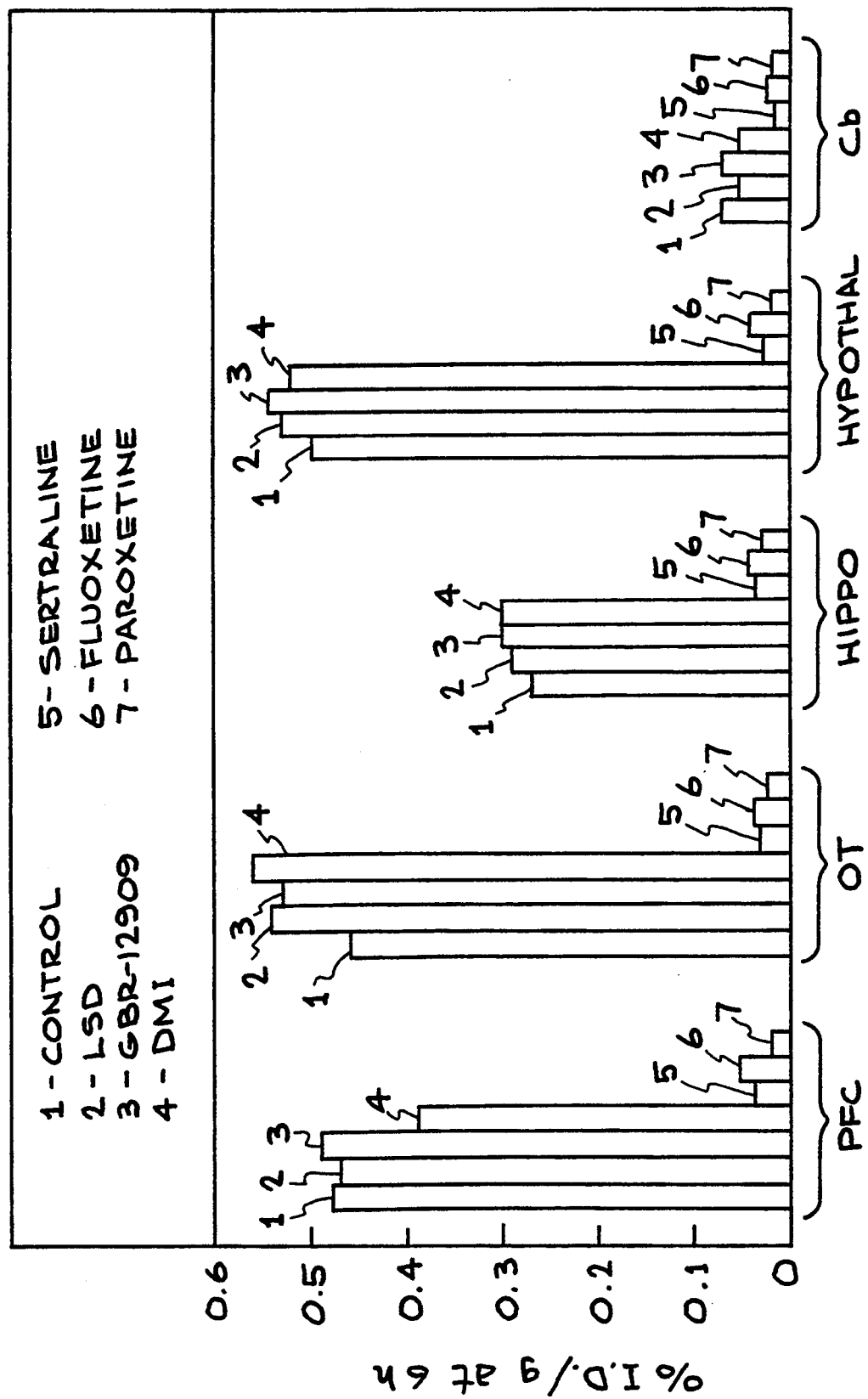
FIG. 6 Shows in vivo competition of drugs on the radioactivity concentration in rat brain regions at 6 h post co-injection with 5-$^{125}$I-6-NQP (total regional radioactivity in the region in terms of percent injected dose per g). Ctrl refers to control rats and all other abbreviations are as defined in FIG. 3.

Blocking studies utilizing a variety of drugs resulted in the demonstration of pharmacologically selective in vivo binding in rats (FIG. 6). Co-injection of 2 mg/kg of specific 5-HT reuptake inhibitors such as sertraline, fluoxetine and paroxetine greatly reduced radioactivity in the prefrontal cortex, olfactory tubercles, hippocampus and hypothalamus at 6 h, but led to only a small change in radioactivity in the cerebellum. Co-injection with 0.5 mg/kg LSD (5-HT$_{1c,2}$agonist), 2mg/kg GBR-12909 (dopamine reuptake inhibitor), and 2 mg/kg DMI (norepinephrine uptake inhibitor) had little effect on radioactivity concentrations in these regions. These results clearly demonstrate the in vivo pharmacological selectivity of 5-$^{125}$I-6-NQP binding to the 5-HT reuptake complex.

Neurotoxin Studies

Figure 7:
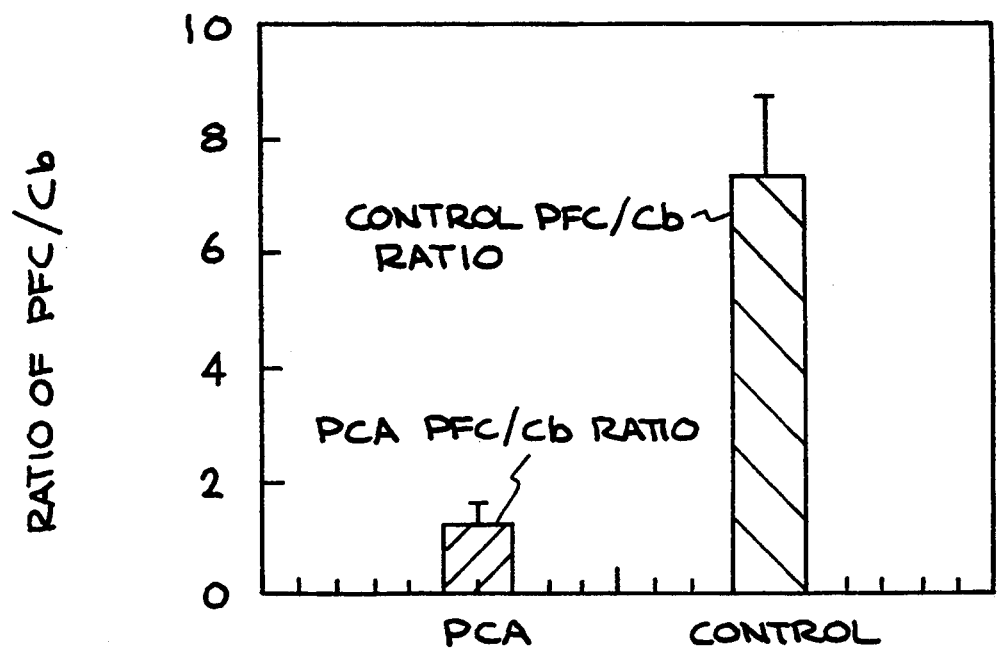
FIG. 7 Is a comparison of the ratios of % ID/g in prefrontal cortex (PFC) and cerebellum (Cb) in control and PCA treated rats at 6 h post injection 5-$^{125}$I-6-NQP (n=3 PCA and n=6 for controls).

Additional studies involving the pretreatment of rats with the selective serotonergic neurotoxin p-chloroamphetamine (PCA; Kohler et al., 1978), at doses of 10 mg/kg for 2 days and then an i.v. injection of 5-$^{125}$I-6-NQP two weeks later, resulted in a regionally selective reduction of specifically bound radioactivity (FIG. 7). The in vivo results were consistent with the reduction in B$_{max}$ measured by in vitro binding methods and indicated up to a 90% reduction in 5-HT reuptake site densities in lesioned rats.

Metabolite Determinations

The brains of rats which had been injected with 25 µCi of 5-$^{125}$I-6-NQP 6 h earlier were removed, homogenized, and repeatedly extracted with ethyl acetate and added cold 5-I-6-NQP carrier. The ethyl acetate fractions were pooled and evaporated, and the concentrate subject to TLC and HPLC (with fraction collection) analyses to determine metabolites in the brain. Our procedures resulted in ~90% of the radioactivity being extracted into the organic phase, and this radioactivity was found to be >98% unmetabolized 5-$^{125}$I-6-NQP. From the amount of radioactivity in the thyroid gland of rats at 6 h post injection (11% of the injected dose), indications are that metabolic deiodination of 5-$^{125}$I-6-NQP occurs in vivo in rats.

Ex Vivo Autoradiography

Ex vivo autoradiography was performed on rats injected with 25 μCi 5-$^{125}$I-6-NQP and killed at 2, 6 and 12 h post injection. Additional autoradiography studies were performed in rats co-injected with 2 mg/kg paroxetine and 5-$^{125}$I-6-NQP as well as in rats treated with the neurotoxin PCA (FIG. 7). In all ex vivo autoradiographic studies, 5-$^{125}$I-6-NQP binding in rat brain was consistent with the known neuroanatomical distribution of the 5-HT reuptake complex and confirmed the microdissection study conclusions described above. These results are in sharp contrast to those obtained with [$^3$H] paroxetine where we found the microdissection technique results to be misleading.

We claim:

1. In a method for measurement of serotonin uptake sites in a sample, in which a radioligand is incubated with a sample and then the radioactivity of the radioligand bound to the sample is determined, the improvement comprising using a radiolabeled substituted 6-nitroquipazine having the formula

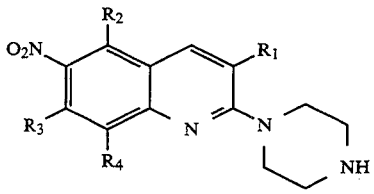

wherein $R_1$, $R_2$, $R_3$, and $R_4$ are each selected from the group consisting of H, Fl, Cl, Br, I, CF$_3$, CH$_2$CH$_2$F, CH$_3$, CH$_2$CH$_3$, and —CH(CH$_3$)$_2$, wherein at least one of $R_1$, $R_2$, $R_3$, and $R_4$ is other than H, and at least one of $R_2$, $R_3$, or $R_4$ is radiohalogenated.

2. The method of claim 1, wherein $R_1$ is H, $R_2$ is Br, $R_3$ is H, and $R_4$ is H.

3. The method of claim 1, wherein $R_1$ is H, $R_2$ is I, $R_3$ is H and $R_4$ is H.

4. The method of claim 3, wherein I is $^{125}$I, or $^{123}$I.

5. The method of claim 1, wherein $R_1$ is H, $R_2$ is F, $R_3$ and $R_4$ are H.

6. The method of claim 1, wherein $R_1$ is H, $R_2$ is CH$_2$CH$_2$F, $R_3$ and $R_4$ are H.

7. The method of claim 1, wherein in the compound $R_1$ is H, $R_2$ is H, $R_3$ is Br and $R_4$ is H.

8. The method of claim 1, wherein in the compound $R_1$ is H, $R_2$ is H, $R_3$ is H and $R_4$ is Br.

9. A radioligand for measuring serotonin uptake sites, which contains a radiolabeled substituted 6-nitroquipazine having the formula

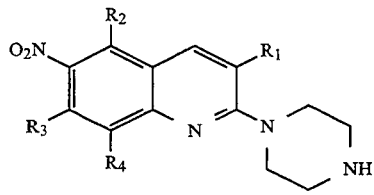

wherein $R_1$, $R_2$, $R_3$, and $R_4$ are each selected from the group consisting of H, Fl, Cl, Br, I, CF$_3$CH$_2$CH$_2$F, CH$_3$, CH$_2$CH$_3$, and —CH(CH$_3$)$_2$, wherein at least one of $R_1$, $R_2$, $R_3$, and $R_4$ is other than H, and at least one of $R_2$, $R_3$, or $R_4$ is radiohalogenated.

10. The compound of claim 9, wherein $R_1$ is H, $R_2$ is Br, $R_3$ is H, and $R_4$ is H.

11. The compound of claim 9, wherein $R_1$ is H, $R_2$ is I, $R_3$ is H and $R_4$ is H.

12. The compound of claim 11, wherein I is $^{125}$I.

13. The compound of claim 9, wherein $R_1$ is H, $R_2$ is F, $R_3$ and $R_4$ are H.

14. The compound of claim 9, wherein $R_1$ is H, $R_2$ is CH$_2$CH$_2$F, $R_3$ and $R_4$ are H.

15. The compound of claim 9, wherein $R_1$ is H, $R_2$ is H, $R_3$ is Br, $R_4$ is H.

16. The compound of claim 9, wherein $R_1$ is H, $R_2$ is H, $R_3$ is H and $R_4$ is Br.

* * * * *